United States Patent [19]

Bonsall et al.

[11] 4,186,105

[45] Jan. 29, 1980

[54] ANTIOXIDANTS

[75] Inventors: Peter C. Bonsall; James W. Morrison; Eric S. Nicholson; George B. Smith; Kenneth G. Townley, all of Blackley, England

[73] Assignee: Imperial Chemical Industries Limited, London, England

[21] Appl. No.: 817,673

[22] Filed: Jul. 21, 1977

[30] Foreign Application Priority Data

Jul. 21, 1976 [GB] United Kingdom ............... 30360/76

[51] Int. Cl.$^2$ .............................................. C09K 15/32
[52] U.S. Cl. ......................... 252/400 R; 260/570.5 P; 260/45.9 QA; 252/401
[58] Field of Search ........................... 252/400 R, 401; 260/570.5 P, 576, 45.90 A, 804, 809

[56] References Cited

U.S. PATENT DOCUMENTS

| | | | |
|---|---|---|---|
| 1,890,916 | 12/1932 | Semon | 260/884 |
| 3,304,284 | 2/1967 | Cox | 252/401 |
| 3,649,690 | 3/1972 | Wheeler | 252/401 |
| 3,655,559 | 4/1972 | Holt | 252/401 |
| 4,013,720 | 3/1977 | Nicholson et al. | 252/401 |

FOREIGN PATENT DOCUMENTS

2729363  1/1978  Fed. Rep. of Germany ........... 252/401

OTHER PUBLICATIONS

Craig, "Journal of American Chemical Society", vol. 55, pp. 3723–3727 (1933).
Walker, "Formaldehyde", 3rd ed., p. 632 (1964).

*Primary Examiner*—Benjamin R. Padgett
*Assistant Examiner*—J. L. Barr
*Attorney, Agent, or Firm*—Cushman, Darby & Cushman

[57] ABSTRACT

Diphenylamine-formaldehyde containing N,N,N',N'-tetraphenyldiaminomethane as the principal product of reaction is obtained by:

(1) In a first stage, heating together a mixture of diphenylamine and formaldehyde in a molecular ratio of from 3:1 to 1:1.5 at a temperature of up to 110° C. until evolution of water is substantially complete, then in a second stage, (2) heating the resultant mixture at a temperature of from 120° C. to a maximum of 140° C. with exclusion of oxygen or oxidizing agents, and removing water and formaldehyde from the reaction mixture until the proportion of bis-(N,N-diphenylaminomethyl)ether present in the mixture falls to below 10% by weight.

The molten reaction product is preferably converted to a solid product by pouring into a stirred, relatively cool immiscible liquid, and coating the resulting granules with a small amount of magnesium oxide or magnesium carbonate.

12 Claims, No Drawings

ANTIOXIDANTS

This invention relates to antioxidants and is more particularly concerned with a process for the manufacture of antioxidants of the tetraphenyldiaminomethane series.

It is known, e.g. from U.S. Pat. No. 1,890,916 and the Journal of the American Chemical Society, 1933, pages 3723–3727, that N,N,N',N'-tetraphenyldiaminomethane can be obtained by heating formaldehyde wit a substantial excess of diphenylamine in an organic solvent, e.g. benzene, removing the latter and the excess diphenylamine by distillation and subjecting the residue to distillation and/or recrystallisation to obtain the product in sufficient purity to crystallise. The product is an excellent antioxidant for rubbers. However, the cost of normal purification methods such as distillation or recrystallisation raise its overall manufacturing cost to a level which is commercially unacceptable. The product obtained by merely heating the reactants together until water ceases to be evolved,—see, e.g.—German OLS No. 2441477—gives a resinous product which frequently remains in a liquid or semi-liquid condition at ambient temperatures, or at best solidifies to a material with a pitch-like consistency. Such products are difficult to handle or to weigh out accurately for compounding with the unvulcanised rubber and in consequence, this highly effective antioxidant has never become a commercial commodity.

It has now been found that products of improved solidification properties can be obtained by a suitable choice of molecular proportions of the formaldehyde and diphenylamine, together with a set of heating conditions of the mixture, as a result of which some impurities are decomposed and other impurities have their formation considerably diminished. The product obtained by the new process is a mixture of the desired N,N,N',N'-tetraphenyldiaminomethane with diphenylamine with only small amounts of other impurities and in consequence the mixture is also a highly effective antioxidant for rubber.

The new process uses as starting materials a mixture of diphenylamine and formaldehyde in which the molar ratio of diphenylamine: formaldehyde is from at most 3:1 to 1:1.5. In practice, the ratio is unlikely to extend beyond from 2:1 to 1:1.25 for economic reason. The preferred value is from 2:1.1 to 1:1.0.

The formaldehyde used is preferably added to the mixture in the form of paraformaldehyde.

The mixture of reactants, which must be free from traces of oxidising agents or acid, is subjected to a heating cycle in which there are two clearly defined stages.

In the first stage, which can be named the condensation stage, the mixture is heated to a maximum of 110° C., preferably under an atmosphere free from oxygen whilst allowing evolved water to distil from the mixture. If desired, the mixture can be allowed to reflux for a period of time before allowing the water to escape, in which case the inert atmosphere is only necessary during the period in which the water is allowed to escape. It is however usually more convenient to provide the inert atmosphere from the start of the reaction period.

If desired, the reaction can be carried out partly at below 100° C. and partly above, or even wholly below 100° C. if a vacuum is applied to remove the water formed, but since this extends the reaction period, there is no advantage in doing so. The preferred method is to carry out the first stage mainly at a temperature of 100°–110° C.

At the end of the condensation stage of the heating cycle, the mixture contains not only the desired N,N,N',N'-tetraphenyldiaminomethane and excess diphenylamine, but also substantial amounts of an impurity bis(N,N-diphenylaminomethyl)ether which has also been formed by condensation of formaldehyde and diphenylamine. This impurity is decomposed by raising the temperature of the mixture to a minimum of 120° C., whereupon the bis(N,N-diphenylaminomethyl)ether is slowly decomposed, with formation of the desired end-product. The progress of decomposition can be followed by subjecting samples of the reaction mixture to analysis by gas liquid chromatography using 100–120 mesh Celite support carrying 0.5% by weight polyethylene glycol of molecular weight 20,000 and 2% by weight potassium hydroxide as the stationary phase, and advantageously using a programmed temperature control ranging from 120° C. to 220° C.

The second stage of the reaction is carried out at a minimum temperature of 120° C., below which temperature the rate of decomposition of the bis-(N,N-diphenylaminomethyl)ether falls off rapidly. Temperatures above 130° C. can be used, but care must be taken to avoid overheating the mixture, or allowing the access of oxygen or oxidising agents, since at 130° C. or above the formation of an impurity of the formula:

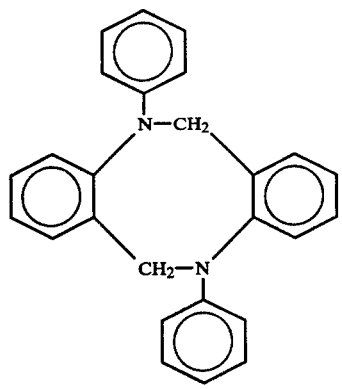

(1)

becomes appreciable, especially if oxygen or oxidising agents such as ferric chloride come into contact with the reaction mixture. Accordingly the second stage is preferably carried out mainly at from 125°–130° C. Reaction should be carried out until the bis-(N,N-dimethylaminoethyl)ether present in the mixture falls to below 10% by weight, preferably below 5% by weight of the mixture. As the original formaldehyde/diphenylamine ratio increases, longer reaction times are required to effect this.

The passage of a stream of inert gas through the mixture, in addition to preventing the access of oxygen, also speeds up the rate of decomposition of the bis-(N,N-diphenylaminomethyl)ether by removing formaldehyde and water which are the by-products of decomposition from the liquid phase to the gas phase and thence out of the system. Other known means for removing volatile materials from the liquid phase to the gaseous phase can be used, e.g. by conducting the reaction at a pressure below atmospheric pressure, optionally with a stream of inert gas through the liquid, or by causing the molten reaction mixture to flow in a thin film within the reactor throughout the reaction period.

At the end of the reaction period, the liquid mixture is capable of solidification on cooling and bandcasting or flaking have been shown to be possible given sufficient cooling. Since the product is a mixture of diphenylamine and the desired tetraphenyldiamino methane, having a low eutectic temperature and capable of forming a readily-ignitable dust, grinding or crushing the solid is an unattractive manufacturing operation. The preferred method of obtaining a solid product is by pouring the molten reaction product into a stirred, relatively cool immiscible liquid, from which it may be recovered as granules by centrifuging, decantation or filtration. A particularly suitable form of liquid is an aqueous solution of an alkali metal salt of a long chain alkane, alkene or poly-cycloaliphatic carboxylic acid especially sodium stearate or sodium rosinate containing up to 1% by weight, and preferably from 0.05 to 0.2% by weight, of the salt.

In isolating in this manner it is found e.g. that by pouring the molten product having a temperature of about 90° C. into not less than 4 times, preferably not less than 7.5 times, its weight of such a solution having an initial temperature of 18° C. or below, the maximum temperature attained by the liquid is 35° C. and smooth, near-spherical, granules can be obtained by stirring until the globules have solidified, and then neutralising the aqueous liquor.

It is also possible to allow the aqueous phase to heat up to higher temperatures, during the mixing, since the liquid globules so obtained solidify to suitable particles as the aqueous phase cools. Usually, however, lower temperature rises are preferred.

As an alternative to the alkali metal salts mentioned above, there can be used from 1 to 10% by weight of partial esters of glycerol with fatty acids as obtained, e.g. by heating castor oil with glycerol under conditions whereby ester interchange takes place.

This process of granulation forms a further feature of the invention.

Yet a further feature of the invention is concerned with prevention of granules obtained by the process from coalescing together on storage to form larger conglomerates of particles. It has been found that treatment of the granules with magnesium oxide or carbonate powder is especially effective for this purpose. The amount of magnesium compound used can be from 5 to 40% by weight, based on the weight of the granules, and preferably should be about 10-15% by weight. Both the so-called "light" and "heavy" grades of these powders can be used. The magnesium compound can be mixed with granules by standard mixing techniques, e.g. by rotation in a tumbler mixer for up to several hours.

The invention is illustrated by the following Examples in which parts and percentages are by weight.

EXAMPLE 1

A mixture of 338 parts of diphenylamine and 35.4 parts of paraformaldehyde are charged to a glass vessel fitted with stirrer, reflux condenser, thermometer and gas inlet tube. The mixture is stirred and heated to 100° C. and nitrogen gas is slowly passed through the molten mass. After 1 hour at 100° C., the condenser is removed and the mixture is heated to 110° C. over a period of 1 hour, by which time there appeared to be no further evolution of water. At this point, a sample of the mixture was found to contain 43.1% of diphenylamine, 19.5% of tetraphenyldiaminomethane and 24.2% of bis-(diphenylaminomethyl)ether.

The mixture was then heated to 120° C. and stirred at this temperature, still maintaining the flow of nitrogen, and periodically taking samples for analysis. After 12½ hours the mixture contained 23.3% diphenylamine, 70.9% tetraphenyldiaminomethane and none of the ether. By continuing to 22 hours at 120° C., the composition of the mixture had changed slightly to 20.5% diphenylamine and 77.7% tetraphenyl diaminomethane.

EXAMPLE 2

This was carried out in a similar manner to Example 1 except that the nitrogen flow was stopped after 2 hours at 120° C. The product contained 24.7% diphenylamine and 68.3% tetraphenyldiaminomethane.

1.5 parts of stearic acid were suspended in 1500 parts of water and sufficient caustic soda solution was added to give a pH of 12. The solution was stirred at 800 rpm and 200 parts of the above product at 90° C. were poured in a thin stream during 30 seconds. Stirring was continued for about 20 minutes, then sufficient acetic acid was added to give a pH of 7. The granules were filtered off and dried at room temperature overnight.

50 Parts of the granules were mixed with 5 parts of magnesium oxide and tumbled in a mill for 16 hours. The treated granules and a sample of untreated granules were subjected to a consolidation test as follows:

12 grams of the granules are placed in a 13 cm×4.5 cm diameter flat-bottomed glass tube and a polythene covered lead weight of 800 g which is a close sliding fit is placed on top of the granuled. The tube is then placed in an oven at 36° C. for seven days. At the end of this time, the lead weight is removed and the granules are checked for free movement. Whereas the untreated granules had consolidated together, the treated granules still flowed freely.

EXAMPLE 3

A mixture of 338 parts of diphenylamine and 45 parts of paraformaldehyde are stirred and heated under nitrogen as in Example 1, giving 1 hour at 100° C. under reflux, a further hour raising to 110° C. and then raising to 130° C., ceasing the nitrogen flow after 1½ hours at this temperature. After 24 hours the bis(diphenylaminomethyl)ether content had dropped to less than 1% and the product contained 16.7% diphenylamine and 76.4% tetraphenyldiaminomethane.

EXAMPLE 4

This was a repeat of Example 1, but heating at 140° C. for the second stage. The bis-(diphenylamino methyl)ether content had dropped to below 1% in 5½ hours at 140° C., and the product contained 30% diphenylamine and 60% tetraphenyldiaminomethane. On continuing heating for a further 15½ hours the figures had changed to 33% and 52% respectively.

If the nitrogen flow was stopped shortly after raising to 140° C. a completely different product was obtained. This contained 39% of diphenylamine and no tetraphenyldiaminomethane. It contained 40% of the product of formula (1) (i.e. 5,11-diphenyl-5,6,11,12-tetrahydrodibenzo-[b,f]-[1,5]diazocine). A similar result was obtained by heating at 130° C. open to the air and in the presence of mild steel.

EXAMPLES 5 to 8

Mixtures of diphenylamine and paraformaldehyde, in the proportions given below are stirred at 100° C. for 3 hours with a slow stream of nitrogen bubbling through the reaction mass. The temperature is then raised to 120° C. and heated for 21 hours at this temperature, the flow of nitrogen being maintained throughout the reaction period. In each case the final reaction mixture, the amounts of which are given below, could be successfully granulated as in Example 2.

| Ex. | Ratio DPA/CH$_2$O | DPA % | —C—CH$_2$-cpd % | —CH$_2$—O—CH$_2$ % |
|---|---|---|---|---|
| 5 | 2/1.0 | 28.0 | 68.5 | 1.0 |
| 6 | 2/1.18 | 29.3 | 66.5 | 2.3 |
| 7 | 2/1.8 | 12.0 | 78.7 | 4.3 |
| 8 | 2/0.7 | 51.6 | 49.5 | 0 |

EXAMPLE 9

A mixture of 338 parts of diphenylamine and 35.4 parts of paraformaldehyde was stirred and heated under nitrogen as in Example 1. After giving 3 hours at 105° C. under reflux the pressure was reduced to 55 mm.Hg. and the temperature was raised to 120° C. for 1 hour. The mixture was held at 70° C. overnight with a stream of nitrogen through, and then had the following composition:
diphenylamine: 31.8%
tetraphenyldiaminomethane: 41.1%
bis(N,N,-diphenylaminomethyl)ether: 18.5%.

A portion of this material was transferred to a rotary evaporator flask and heating continued at 120° C. under 50 mm.Hg. pressure (Material A), while the remainder of the material was also heated at 120° C. under 50 mm.Hg. pressure in the original vessel (Material B).

The bis(N,N-diphenylaminomethyl)ether content of Material A had dropped to 8.5% after 4 hours treatment and to 4.6% after 7 hours. The bis(N,N-diphenylaminomethyl)ether content of Material B was 15.8% and 13.4% after the same intervals of time.

EXAMPLE 10

300 Kilos of diphenylamine and 32 kilos of paraformaldehyde are charged to an enamelled cast iron vessel fitted with stirrer, thermometer pocket, inert gas inlet, and reflux condenser. The mixture is stirred and brought to 100°–105° C. while a slow stream of nitrogen is passed through the molten mass. After 3 hours refluxing at 100°–105° C. the unit is set for distillation and water distilled out, the temperature rising to 110° C. The material at this point contains 35.1% of diphenylamine, 24.2% of tetraphenyldiaminomethane, and 28.2% of bis(N,N-diphenylaminomethyl)ether.

A vacuum of 75 mm.Hg. is applied to the vessel, still maintaining a slow stream of nitrogen through the molten material. The material is stirred and heated at 125°–130° C. for 12 hours when a sample has the composition 22.5% of diphenylamine, 74.0% of tetraphenyldiaminomethane and 2.3% of bis(N,N-diphenylaminomethyl)ether. Heating at 125°–130° C. is continued for a further 17 hours and the mixture, whose composition is virtually unchanged from the 12 hour sample, is cooled to 92° C. and blown with nitrogen over a few minutes into 7.5 times its weight of 0.2% sodium stearate solution held at 28° C.

Granules of solid are formed within a few minutes, the final temperature reached being 32° C. The aqueous slurry is neutralised with acetic acid and filtered. The granules are dried to a water content of 1.7%, and coated with light magnesium oxide (7.5% addition based on weight of granules) by tumbling the materials together for ½ hour. Near spherical granules are obtained, which show no signs of coalescence when subjected to a consolidation test as described in Example 2.

What we claim is:

1. A process for the manufacture of diphenylamine-formaldehyde reaction products containing N,N,N',N'-tetraphenyldiaminomethane as the principal product of reaction, which reaction comprises:
    (1) In a first stage, heating together a mixture of diphenylamine and formaldehyde in a molecular ratio of from 3:1 to 1:1.5 at a temperature of up to 110° C. until evolution of water is substantially complete, then in a second stage,
    (2) heating the resultant mixture at a temperature of from 120° C. to a maximum of 140° C. with exclusion of oxygen or oxidising agents, and removing water and formaldehyde from the reaction mixture until the proportion of bis,(N,N-diphenylaminomethyl)ether present in the mixture falls to below 10% by weight.

2. A process as claimed in claim 1 wherein the ratio of diphenylamine to formaldehyde is from 2:1 to 1:1.25.

3. A process as claimed in claim 2 wherein the ratio of diphenylamine to formaldehyde is from 2:1.1 to 1:1.0.

4. A process as claimed in claim 1 wherein the formaldehyde used is in the form of paraformaldehyde.

5. A process as claimed in claim 1 wherein the first stage is carried out mainly at a temperature of 100°–110° C.

6. A process as claimed in claim 1 wherein the second stage is carried out mainly at a temperature of 125°–130° C.

7. A process as claimed in claim 1 wherein the second stage reaction is carried out until the bis-(N,N-dimethylaminomethyl)ether content falls to below 5% by weight.

8. A process as claimed in claim 1 wherein the molten reaction product is converted to solid granules by pouring into a stirred, relatively cool immiscible liquid.

9. A process as claimed in claim 8 wherein the liquid is an aqueous solution containing up to 1% by weight of sodium stearate or sodium resinate.

10. Solid granules of diphenylamine-formaldehyde reaction products produced by the process claimed in claim 8.

11. A process for stabilising the physical form of the solid granules claimed in claim 10, which comprises treating the granules with from 5 to 40% by weight, based on the weight of the granules, of magnesium oxide or magnesium carbonate.

12. Stabilised granules of diphenylamine-formaldehyde reaction products produced by a process claimed in claim 11.

* * * * *